United States Patent [19]

Wilson

[11] Patent Number: 4,931,085
[45] Date of Patent: Jun. 5, 1990

[54] HERBICIDAL COMPOSITION

[75] Inventor: Donald Wilson, Midhurst, England

[73] Assignee: Imperial Chemical Industries PLC, London, England

[21] Appl. No.: 338,399

[22] Filed: Apr. 14, 1989

Related U.S. Application Data

[63] Continuation of Ser. No. 6,852, Jan. 27, 1987, abandoned.

[30] Foreign Application Priority Data

Jan. 27, 1986 [GB] United Kingdom ................ 8601869

[51] Int. Cl.$^5$ ............................................ A01N 43/48
[52] U.S. Cl. ...................................................... 71/92
[58] Field of Search ............................................ 71/92

[56] References Cited

FOREIGN PATENT DOCUMENTS 0326409 12/1975 Austria ..................................... 71/92
363714 8/1981 Austria .
363715 8/1981 Austria .

Primary Examiner—Richard L. Raymond
Assistant Examiner—Raymond Covington
Attorney, Agent, or Firm—Cushman, Darby & Cushman

[57] ABSTRACT

A herbicidal preparation comprising a compound of formula (I):

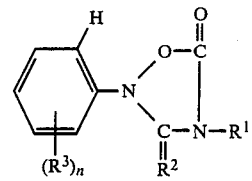

wherein $R^1$ is $C_{1-3}$ alkyl or $C_{2-3}$ alkenyl; $R^2$ is oxygen or sulphur, $R^3$ is halogen, lower alkyl, lower alkenyl, lower haloalkyl, lower alkoxy, nitro, amino, lower alkylamino, lower dialkylamino, lower alkylthio, lower alkylsulphoxide, lower alkylsulphone, cyano or thiocyano; and n is zero or an integer up to 4; provided that when n is greater than 2 a maximum of two $R^3$ groups are selected from nitro, amino, lower alkylamino and lower dialkylamino, in combination with a compound of formula (II):

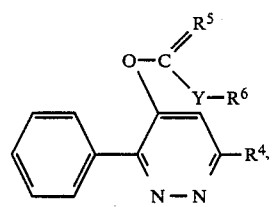

wherein $R^4$ is chlorine or bromine; $R^5$ is oxygen or sulphur; $R^6$ is straight or branched $C_{1-18}$ alkyl or phenyl; and Y is sulphur or when $R^5$ is sulphur, Y may be oxygen.

4 Claims, No Drawings

HERBICIDAL COMPOSITION

This is a continuation of Application No. 07/006,852, filed Jan. 27, 1987, now abandoned.

This invention relates to a herbicidal treatments and compositions using a synergistic mixture of at least two herbicides.

U.S. Pat. No. 3,437,664 discloses herbicidal compounds of formula (I):

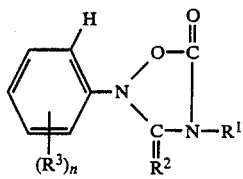
(I)

wherein $R^1$ is $C_{1-3}$ alkyl or $C_{2-3}$ alkenyl; $R^2$ is oxygen or sulphur, $R^3$ is halogen, lower alkyl, lower alkenyl, lower haloalkyl, lower alkoxy, nitro, amino, lower alkylamino, lower dialkylamino, lower alkylthio, lower alkylsulphoxide, lower alkylsulphone, cyano or thiocyano; and n is zero or an integar up to 4; provided that when n is greater than 2, a maximum of two $R^3$ groups are selected from nitro, amino, lower alkylamino and lower dialkylamino.

The term "lower" as used herein means up to about 10 carbon atoms.

Austrian Patent No. 326409 discloses herbicidal compounds of formula (II):

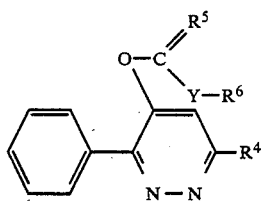
(II)

wherein $R^4$ is chlorine or bromine; $R^5$ is oxygen or sulphur; $R^6$ is straight or branched $C_{1-18}$ alkyl group, or phenyl and Y is sulphur or when X is sulphur, Y may also be oxygen.

The applicants have found that the application of a mixture of a compound of formula (I) in combination with a compound of formula (II) produces a greater herbicidal effect against weed species than would be expected taking into account the activities of each of the compounds alone, and does not adversely affect the photoxicity towards the crop species.

According to the present invention there is provided a herbicidal preparation comprising a compound of formula (I) as hereinbefore defined and a compound of formula (II) as hereinbefore defined.

Compounds of formula (I) and (II) may be prepared as described in U.S. Pat. No. 3,437,644 and Austrian Patent No. 326409 respectively.

A preferred compound of formula (I) is methazole of formula (IA):

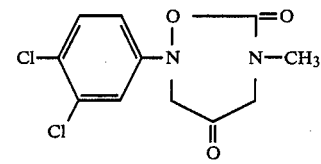
(IA)

A preferred compound of formula (II) is pyridate of formula (IIA):

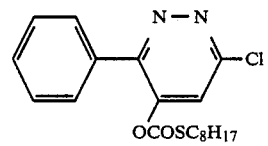
(IIA)

The preparations of the invention have useful herbicidal activity. They are capable of controlling the growth of a variety of plants including broad-leafed and grassy weed species in a wide range of situations such as agriculture and horticulture, forestry and amenity. They may be used on a wide range of crops such as cereals, rice, maize, oilseed crops, peanuts, soya, sunflowers and many vegetables, for example, peas, beans, tomatoes, onions, brassicas and potatoes.

Depending upon the particular compounds of formula (I) and (II) employed, the compounds can be applied to the above ground parts of growing plants (post-emergence application) or to the soil prior to germination of the plants (pre-emergence application). One useful application mode in crops such as potatoes is to apply the compounds to the weeds post-emergently but before the germination of the crop.

In another aspect therefore, the invention provides a Process of inhibiting the growth of unwanted plants, by applying to the plants, or to the locus thereof, a compound of formula (I) as hereinbefore defined and a compound of formula (II) as hereinbefore defined.

The rate of application required to inhibit the growth of unwanted plants will depend on, for example, the particular compounds of formulae (I) and (II) chosen for use, and the particular species of plant the composition is desired to control. However, as a general guide, an amount of from 0.1 to 4.0 kilograms preferably from 0.25 to 2.0 kilograms total active ingredient per hectare, is usually suitable. The ratio of the compound of formula (I) to the compound of formula (II) applied is suitably in the range of from 3:1 to 1:3 preferably from 2:1 to 1:2.

The compounds of formulae I and II are suitably administered in the form of compositions.

Further according to the present invention there is provided a herbicidal composition comprising a compound of formula (I), a compound of formula (II) and a solid or liquid diluent.

A particularly preferred composition is a composition comprising compound (IA) as hereinbefore defined and a compound of formula (IIA) as hereinbefore defined in combination with a solid or liquid diluent. The ratio of compound (IA):(IIA) in the composition is preferably in the range of from 0.7:1 to 1.6:1.

This composition has been found to be particularly useful in post-emergence application to brassicas and onions.

Preferably the composition also comprises a surface active agent.

The compositions of the invention may be solid compositions in the form of dispersible powders or grains comprising in addition to the active ingredient, a wetting agent to facilitate the dispersion of the powder or grains in liquids. Such powders or grains may include fillers, suspending agents and the like.

Liquid compositions include solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general, concentrates may conveniently contain from 10 to 90% and preferably from 25 to 90% by weight of active ingredient. Dilute preparations ready for use may contain varying amounts of the active ingredient, depending upon the purpose for which they are to be used; however, dilute Preparations suitable for many uses contain between 0.01% and 10% and preferably between 0.1% and 1% by weight of the active ingredient.

The preparation of the invention is preferably presented in a single composition. However they may be presented in a two pack-container, one compartment of which containing a composition comprising a compound of formula (I) in combination with a solid or liquid diluent and the second compartment contains a composition comprising a compound of formula (II) in combination with a solid or liquid diluent.

The contents of the two compartments can then be admixed, for example by dissolving both in aqueous solution prior to administration.

The compositions of the invention can be used in association with another herbicide, for example in the form of a mixture or in a composition of the invention.

The other herbicide will generally be a herbicide having a complementary action, depending upon the particular utility and circumstances of administration.

Examples of useful complementary herbicides are:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (eg. salts, esters and amides);

C. 3-[4-(4-halophenoxy)phenyl]-1,1-dialkylureas such as 3-[4-(4-chlorophenoxy)phenyl]-1,1-dimethylurea.

D. Dinitrophenols and their derivatives (eg. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);

F. phenylurea herbicides such as N'-(3,4-dichlorophenyl)-N,N-dimethylurea (diuron) and N,N-dimethyl-N'-[3-(trifluoromethyl)phenyl]urea (flumeturon);

G. phenylcarbamoyloxyphenylcarbamates such as 3-[methoxy carbonylamino]phenyl (3-methylphenyl)-carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyl-uracil (bromacil) and 3-t-butyl-5-chloro-6-methyl-uracil (terbacil);

J. triazine herbicides such as 2-chloro-4-ethylamino-6-(i-propylaminio)-1,3,5-triazine (atrazine), 2-chloro4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-pehnylurea herbicides such as 3(3,4-dichlorophenyl)-1-methoxy-1-methylurea (linuron), 3-(4-chlorophenyl)-1-methoxy-1-methylurea (monolinuron), 3-(4-bromo-4-chlorophenyl)-1-methoxy1-methylurea (chlorobromuron).

L. thiolcarbamate herbicides such as S-propyl dipropylthiocarbamate (vernolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl-chloro-2',6'-fiethylacetanilide (butachlor), the correspondimg N-methoxy compound (alachlor), the corresponding N-i-propyl compound (propachlor), 3',4'-dichloropropionanilide (propanil) and 2-chloro-N-[pyrazol-1-ylmethyl]acet-2'-6'-xylidide (metazachlor);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4- trifluoromethylphenoxy)benzoic acid (acifluorfen) and salts and esters thereof, 2-chloro-4-trifluoromethylphenyl 3-ethoxy-4-nitrophenyl ether (oxyfluorfen) and 5-(2-chloro-4-(trifluoromethyl)phenoxy)-N-(methylsulfonyl)-2-nitrobenzamide (fomesafen); and S. phenoxyphenoxypropionate herbicides such as 2-(4-(4'-trifluoromethylphenoxy)-phenoxy)-propionic acid methylester (trifop-methyl), 2-(4-((5-trifluoromethyl)2-(pyridinyl)oxy)phenoxypropanoic acid (fluazifop) and esters thereof, 2-(4-((3-chloro-5-trifluoromethyl)-2-pyridinyl)oxy)phenoxy)propanoic acid (haloxyfop) and esters thereof, 2-(4-((6-chloro-2-quinoxalinyl)oxy)phenoxypropanoic acid (xylofop) and esters thereof; and T. cyclohexanedione herbicides such as 2,2-dimethyl-4,6-dioxo-5-(1-((2-propenyloxy)amino)-butylidine) cyclohexane carboxylic acid (alloxydim) and salts thereof, 2-(1-ethoxyimino)butyl-5-(2-(ethylthio)propyl)-3-hydroxy-2-cyclohexene-1-one (sethoxydim), 2-(1-(3-chloroallyloxyimino)butyl)-5-(2-ethylthiopropyl)-3-hydroxy cyclohex-2-enone (cloproxydim), 2(1-ethoxyimino)butyl)-3-hydroxy-5-thian-3-yl cyclohex-2-enone (cycloxydim); and U. sulfonyl urea herbicides such as 2-chloro-N-(4-methoxy-6-methyl-1,3,5-triazin-2-yl)-aminocarbonyl) benzenesulphonamide (chlorsulfuron), methyl 2(4,6-dimethyl-2-pyrimidinyl)amino)carbonyl)amino)sulphonyl)benzoic acid (sulfometuron), 2-((((3-(4-methoxy-6-methyl-1,3,5-triazin-2-yl)carbonyl)amino)sulphonyl)benzoic acid (metsulfuron) and esters thereof;

V. imidazolidinone herbicides such as 2-(4,5-dihydro-4-isopropyl-4-methyl-5-oxoimidazol-2-yl)quinoline-3carboxylic acid (imazaquin), methyl 6-(4-isopropyl-4-methyl-5-oxo-2-imidazolin-2-yl)-M-toluate and P-toluate isomer (AC 222293)

W. arylanilide herbicides such as 1-methylethyl-N-benzoyl-N-(3-chloro-4-fluorophenyl)-L-alanine (flamprop-isopropyl), ethyl N-benzoyl-N-(3,4-dichlorophenyl)-DL-alaninate (benzoylprop-ethyl), N-(2,4-difluorophenyl)-2-(3-(trifluoromethyl)-phenoxy)-3-pyridinecarboxamide (diflufenican); and X. amino acid herbicides such as N-(phosphonomethyl)glycine (glyphosate) and DL-homoalanin-4-yl(methyl)phosphinic acid (phosphinothricin) and their salts and esters; and Y. organoarsenical herbicides such as monosodium methanearsonate (MSMA); and Z. miscellaneous herbicides including N,N-dimethyldiphenylacetamide (diphenamid), N-(1-naphthyl)phthalamic acid (naptalam) and 3-amino-1,2,4-triazole, 2-ethoxy-2,3-dihydro-3,3-dimethylbenzofuran methanesulfonate (ethofumesate), 1,4-epoxy-p-meth-2yl 2-methybenzyl ether (cinmethylin);

AA. Examples of useful contact herbicides include: bipyridylium herbicides such as those in which the active entity is the 1,1'-dimethyl-4,4'-dipyridylium ion (paraquat) and those in which the active entity is the 1,1'-ethylene-2,2'-dipyridlium ion (diquat);

The following example illustrates the invention.

EXAMPLE 1

The following trials were carried out using an aqueous suspension of a wettable powder containing 75% methazole (Compound 1A obtained from Velsicol Chemical Corporation) and an aqueous suspension of a wettable powder containing 45% pyridate (Compound IIA as hereinbefore defined obtained from Chemie Linz Aktiengesellschaft).

Treatments were applied post weed and crop emergence.

Test crops used and varieties were:

| Brussels sprouts | Variety - Bedford Darkmar 21 |
| --- | --- |
| Cabbage | Variety - Buderich |
| Cauliflower | Variety - Perfection |
| Peas | Variety - Verdette |
| Onion | Variety - Domino F1 |

These were drilled as single rows in a five row bed system. At the time of applying the herbicides, the test crops were at growth stages:

| Brassica | 3 and 4 true leaves |
| --- | --- |
| Onions | 2 to 3 leaves |
| Peas | 3 to 5 stipules |

The growth stages of the weeds varied from cotyledon to 4 to 5 inches in height. The weed spectrum and population was uniform prior to the administration of the herbicide.

In order to carry out the test, a matrix system was employed whereby suspensions of methazole and pyridate were applied individually along the rows at various rates. Further suspensions of methazole and pyridate were then applied across the beds, again at various rates to maximise the combination under test. The suspensions were applied using a knapsack sprayer with hand held boom and pressurised with $CO_2$ or propane. The size of each plot was two meters by two meters.

After thirteen days, the plots were assessed for weed control and crop phytotoxicity.

The weed control was assessed by counting the weed species per square meter. This was then expressed as a Percentage of the number of seedlings in an untreated control area (318 weed seedings/m²). Types of weeds found included chickweed (*Stellaria media*), fat-hen (*Chenopodium album*), groundsel (Senecio vulgaris), knot-grass (*Polygonum aviculare*), black nightshade (*Solanum nigrum*) and annual meadow grass (*Poa annua*). No significant difference in crop phytoxicity was observed over all treatments.

The results are given in Table I.

TABLE I

| Treatments | g ai/ha | % Total Weed Control (No/m²) | | | | | |
| --- | --- | --- | --- | --- | --- | --- | --- |
| | | | | Methazole | | | |
| | | Nil | 375 | 562 | 750 | 1124 | 1500 |
| Pyridate | Nil | (318) | 35 | 25 | 33 | 57 | 74 |
| | 540 | 40 | 69 | 94 | 86 | — | — |
| | 810 | 52 | 79 | 96 | 92 | — | — |
| | 1080 | 61 | 87 | 94 | 92 | — | — |
| | 1620 | 76 | — | — | — | — | — |
| | 2160 | 94 | — | — | — | — | — |

EXAMPLE 2

The following trials were carried out using similar aqueous suspensions to those described in Example 1.

Treatments were applied post weed and crop emergence.

Test crops used and varieties were:

| Tr1 | Cauliflower | Variety - Barrier Reef |
| --- | --- | --- |
| Tr2 | Cabbage | Variety - Golden Cross |

In Trial 1 (Tr 1) the cauliflower crops were transplanted from a seed bed into the soil just prior to the trial. In Trial 2 (Tr 2) the cabbages were directly drilled and were at growth stage 4–5 leaves at the time of the trial.

Trials were conducted on a replicated randomised plot design with six replicates. Treatments comprised the application of suspensions of methazole and pyridate either alone or in tank mixture.

The suspensions were applied using a knapsack sprayer with hand held boom and pressurised with $CO_2$ or Propane.

Each plot comprised 4 crop rows and was 8–10 m in length.

After twenty-one days, the plots were assessed for weed control and crop phytotoxicity.

The weed control was assessed by counting the weed species per square meter.

The results are given in Table II.

TABLE II

| Treatment g ai/ha | No. of weeds in 21 days after treatment | | Crop Vigour 0–10 scale* | |
| --- | --- | --- | --- | --- |
| | Tr 1 | Tr 2 | Tr 1 | Tr 2 |
| Methazole + pyridate 375 + 540 | 0.4 | 42 | 9.8 | 10.0 |
| Methazole + pyridate 562 + 270 | 6.8 | 81 | 9.8 | 10.0 |
| Methazol + pyridate 562 + 360 | 1.0 | 55 | 9.8 | 10.0 |
| Methazole + pyridate 750 + 270 | 0.6 | 52 | 9.4 | 10.0 |
| Methazole 750 | 5.4 | 115 | 9.8 | 10.0 |
| Pyridate 270 | 14.6 | 191 | 10.0 | 10.0 |
| Pyridate 540 | 5.8 | 203 | 9.6 | 10.0 |
| Untreated | 18.8 | 282 | 10.0 | 10.0 |

*Scale 0 = Dead plant, 10 = Full vigour

I claim:

1. A herbicidal composition comprising an effective amount of a compound of formula (IA):

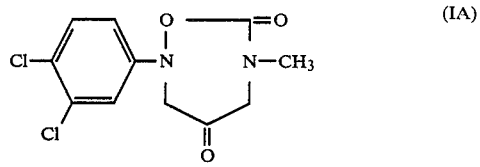

in combination with an effective amount of compound of formula (IIA):

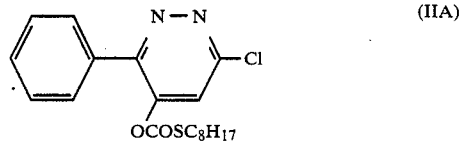

2. A composition according to claim 1 in the ratio of compound IA to IIA of from 3:1 to 1:3.

3. A composition according to claim 1 in the ratio of compound IA to IIA of from 2:1 to 1:2.

4. A process for inhibiting the growth of unwanted plants which comprises applying to the plants, or the locus of the plants, an effective amount of compound (IA) and compound (IIA) as defined in claim 1.

* * * * *